(12) United States Patent
Alenfall et al.

(10) Patent No.: US 8,936,783 B2
(45) Date of Patent: Jan. 20, 2015

(54) **USE OF *LACTOBACILLUS* FOR TREATMENT OF AUTOIMMUNE DISEASES**

(75) Inventors: Jan Alenfall, Lomma (SE); Anna Berggren, Flyinge (SE); Carola Rask, Bunkelfostrand (SE); Agnes Wold, Mölndal (SE); Shahram Aghaibeik-Lavasani, Malmö (SE)

(73) Assignee: Probi AB, Lund (SE)

( * ) Notice: Subject to any disclaimer, the term of this patent is extended or adjusted under 35 U.S.C. 154(b) by 1522 days.

(21) Appl. No.: 11/992,483

(22) PCT Filed: Oct. 6, 2006

(86) PCT No.: PCT/SE2006/001139
§ 371 (c)(1),
(2), (4) Date: May 6, 2009

(87) PCT Pub. No.: WO2007/040446
PCT Pub. Date: Apr. 12, 2007

(65) Prior Publication Data
US 2009/0208469 A1    Aug. 20, 2009

(30) Foreign Application Priority Data

Oct. 6, 2005 (SE) ...................................... 0502209
Oct. 7, 2005 (SE) ...................................... 0502250

(51) Int. Cl.
| | |
|---|---|
| *A01N 63/00* | (2006.01) |
| *A61K 39/02* | (2006.01) |
| *C12N 1/12* | (2006.01) |
| *A23L 1/30* | (2006.01) |
| *A21D 2/26* | (2006.01) |
| *A21D 8/04* | (2006.01) |
| *A21D 13/00* | (2006.01) |
| *A23C 9/123* | (2006.01) |
| *A23L 1/03* | (2006.01) |
| *A23L 1/10* | (2006.01) |
| *A23L 2/52* | (2006.01) |
| *A61K 35/74* | (2006.01) |
| *C12R 1/225* | (2006.01) |
| *C12R 1/25* | (2006.01) |

(52) U.S. Cl.
CPC .............. *A23L 1/3014* (2013.01); *A21D 2/267* (2013.01); *A21D 8/045* (2013.01); *A21D 13/0067* (2013.01); *A23C 9/123* (2013.01); *A23L 1/0345* (2013.01); *A23L 1/10* (2013.01); *A23L 2/52* (2013.01); *A61K 35/747* (2013.01); *C12R 1/225* (2013.01); *C12R 1/25* (2013.01); *A23V 2002/00* (2013.01); *A23Y 2220/73* (2013.01); *Y10S 514/903* (2013.01); *Y10S 435/857* (2013.01); *Y10S 435/853* (2013.01)
USPC ..................... 424/93.45; 424/234.1; 514/903; 435/857; 435/853; 435/252.1

(58) Field of Classification Search
None
See application file for complete search history.

(56) References Cited

U.S. PATENT DOCUMENTS

| | | | |
|---|---|---|---|
| 6,696,057 B1 | 2/2004 | Bojrab | |
| 6,830,750 B1 * | 12/2004 | Naruszewicz | 424/93.45 |
| 7,507,572 B2 * | 3/2009 | Molin et al. | 435/252.9 |
| 7,807,440 B2 * | 10/2010 | Molin et al. | 435/252.1 |
| 2004/0052903 A1 * | 3/2004 | Antonsson et al. | 426/42 |

FOREIGN PATENT DOCUMENTS

| | | |
|---|---|---|
| WO | WO03/022255 A2 | 8/2002 |
| WO | WO2004/076615 A2 | 9/2004 |
| WO | WO2004/087893 A | 10/2004 |
| WO | WO2004/103083 A1 | 12/2004 |

OTHER PUBLICATIONS

Supplementary Partial European Search Report for corresponding Application No. PCT/SE2006001139, dated Jan. 18, 2010.

Schultz, M., et al., *Lactobacillus plantarum* 299V in the Treatment and Prevention of Spontaneous Colitis in Interleukin-10-Deficient Mice, Inflammatory Bowel Diseases, Mar. 2002, pp. 71-80, vol. 8, No. 2.

Pathmakanthan, S., et al., *Lactobacillus plantarum* 299: Beneficial in vitro immunomodulation in cells extracted from inflamed human colon, Journal of Gastroenterology and Hepatology, Feb. 2004, pp. 166-173, vol. 19, No. 2, Wiley Interscience, Melbourne, Australia.

Niedzielin, K., et al., A controlled, double-blind, randomized study on the efficacy of *Lactobacillus plantarum* 299V in patients with irritable bowel syndrome, European Journal of Gastroenterology Hepatology, Oct. 1, 2001, pp. 1143-1147, vol. 13, No. 10.

Fujiwara, D., et al., The Anti-Allergic Effects of Lactic Acid Bacteria Are Strain Dependent and Mediated by Effects on both TH1/Th2 Cytokine Expression and Balance, International Archives of Allergy and Immunology, Oct. 4, 2004, pp. 205-215, vol. 135, No. 3.

Kato, I., et al., Suppressive effects of the oral administration of *Lactobacillus casei* on type II collagen-induced arthritis in DBA/1 mice, Life Sciences, Jul. 17, 1998, pp. 635-644, vol. 63, No. 8.

Lavasani, S., et al., Suppression of experimental autoimmune encephalomyelitis (EAE) by oral administration of *Lactobacillus paracasei* DSM 13434, Gastroenterology, Apr. 2006, p. A99, vol. 130, No. 4, Suppl. 2 (Abstract).

Parra, M.D. et al., "Daily ingestion of fermented milk containing *Lactobacillus casei* DN114001 improves innate-defense capacity in healthy middle-aged people", J. Physiol. Biochem. 2004, vol. 60, No. 2, pp. 85-92.

(Continued)

*Primary Examiner* — S. Devi

(74) *Attorney, Agent, or Firm* — Buchanan Ingersoll & Rooney PC

(57) ABSTRACT

The present technology relates to the use of at least one strain of probiotic bacteria selected from *Lactobacillus* for the manufacture of a medicament for the treatment and/or prevention of an autoimmune disease.

5 Claims, 19 Drawing Sheets

(56) References Cited

OTHER PUBLICATIONS

Bunout, Daniel et al., "Effects of a Nutritional Supplement on the Immune Response and Cytokine Production in Free-Living Chilean Elderly", Journal of Parenteral and Enteral Nutrition 2004, vol. 28, No. 5, pp. 348-354.

Nadia Osman et al., *Modulation of the Effect of Dextran Sulfate Sodium-Induced Acute Colitis by the Administration of Different Probiotic Strains of Lactobacillus and Bifidobacterium,* 49(2) Digestive Diseases and Sciences 320-327 (Feb. 2004).

Thierry von der Weid et al., *Induction by a Lactic Acid Bacterium of a Population of $CD4^+$ T Cells with Low Proliferative Capacity That Produce Transforming Growth Factor $\beta$ and Interleukin-10,* 8(4) Clinical and Diagnostic Laboratory Immunology 695-701 (Jul. 2001).

\* cited by examiner

Fig. 1

|  | Wash out period (Week) | | Study period (Week) | | | | | Post study period (Week) | |
|---|---|---|---|---|---|---|---|---|---|
|  | -2 | -1 | 1 | 2 | 3 | 4 | 5 | +1 | +2 |
| L. plantarum | 0/7 | 1/7 | 3/7 | 2/7 | 3/7 | 2/7 | 1/7 | 1/7 | 0/7 |
| L. Heal 19 | 0/7 | 1/7 | 1/7 | 2/7 | | | | 2/7 | 1/7 |
| L. fermentum | 0/7 | 0/7 | 0/7 | 0/7 | | | | 1/7 | 0/7 |
| L. paracasei | 0/7 | 0/7 | 1/7 | 0/7 | | | | 0/7 | 0/7 |
| L. gasseri | 0/7 | 0/7 | 3/7 | 1/7 | | | | 4/7 | 0/7 |
| L. rhamnosus | 1/7 | 1/7 | 0/7 | 0/7 | | | | 1/7 | 0/7 |
| P. lundensis | 1/6 | 1/6 | 1/6 | 1/6 | | | | 0/6 | 0/6 |
| Placebo | 0/9 | 0/9 | 2/9 | 3/9 | 1/8 | 1/8 | 0/8 | 0/8 | 0/8 |

Fig. 2.

|  | CD4+ T cells (x 10³) | CD8+ T cells (x 10³) | NKT cells (x 10³) |
|---|---|---|---|
| *L. plantarum* | 647 (92) | 318 (37) | 64 (17) |
| *L. Heal 19* | 817 (105) | 328 (43) | 56 (19) |
| *L. fermentum* | 907 (82) | 479 (51) | 87 (21) |
| *L. paracasei* | 794 (87) | 321 (64) | 98 (21) |
| *L. gasseri* | 767 (54) | 497 (110) | 111 (39) |
| *L. rhamnosus* | 775 (109) | 387 (50) | 109 (22) |
| *P. lundensis* | 731 (65) | 468 (84) | 87 (29) |
| Placebo | 650 (43) | 300 (34) | 107 (30) |

Figure 3.

| | % CD4+CD25+ of lymphocytes | % CD8+CD25+ of lymphocytes | % CD4+HLA-DR+ of lymphocytes | % CD8+HLA-DR+ of lymphocytes | GMFI CD45RO on CD4+ T cells | GMFI CD45RO on CD8+ T cells |
|---|---|---|---|---|---|---|
| L. plantarum | 10 (0,90) | 0,83 (0,19) | 4,3 (0,69) | 5,0 (1,8) | 53 (10) | 27 (5,6) |
| L. Heal 19 | 17 (2,6) | 1,5 (0,40) | 4,4 (1,2) | 6,6 (3,3) | 126 (39) | 61 (15) |
| L. fermentum | 15 (0,98) | 1,5 (0,31) | 4,4 (0,51) | 7,0 (1,1) | 71 (13) | 36 (5,6) |
| L. paracasei | 17 (1,1) | 1,7 (0,73) | 8,5 (4,7) | 6,1 (1,6) | 83 (13) | 50 (17) |
| L. gasseri | 15 (2,0) | 1,3 (0,26) | 3,3 (0,60) | 5,2 (1,3) | 110 (96) | 45 (14) |
| L. rhamnosus | 14 (0,60) | 1,3 (0,13) | 3,0 (0,34) | 5,2 (1,3) | 80 (24) | 40 (11) |
| P. lundensis | 18 (4,1) | 4,0 (2,3) | 10 (6,7) | 9,4 (2,4) | 65 (9,4) | 38 (3,5) |
| Placebo | 13 (1,0) | 2,6 (1,4) | 4,2 (0,59) | 6,8 (3,5) | 39 (8,2) | 23 (5,1) |

A
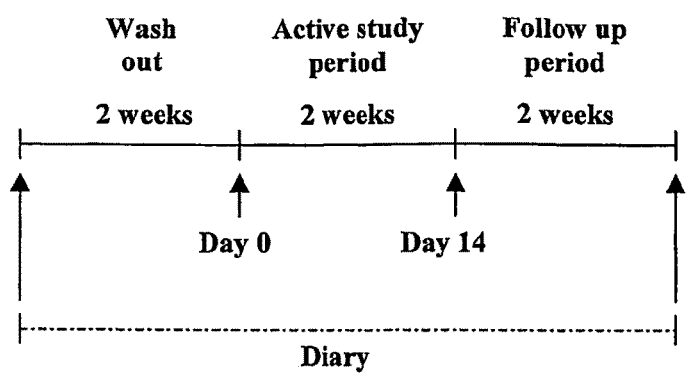
B
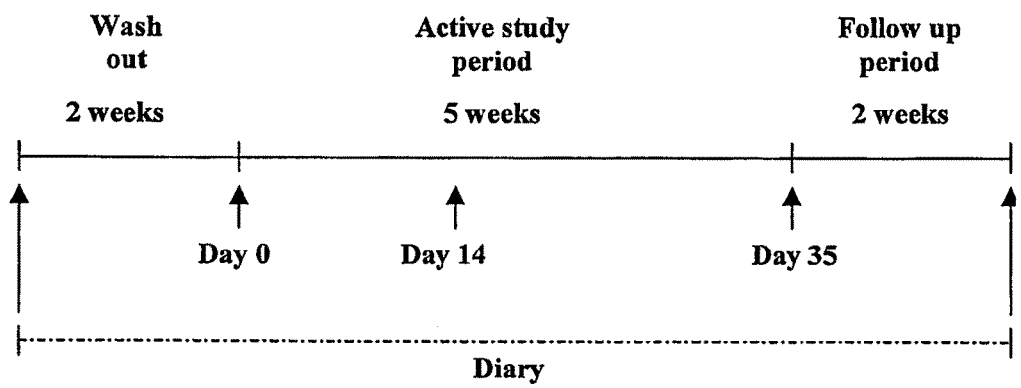
Fig. 4

Fig. 5
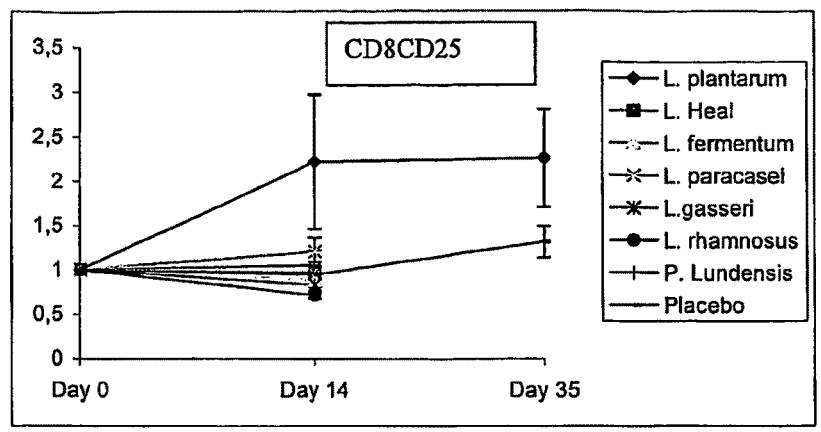
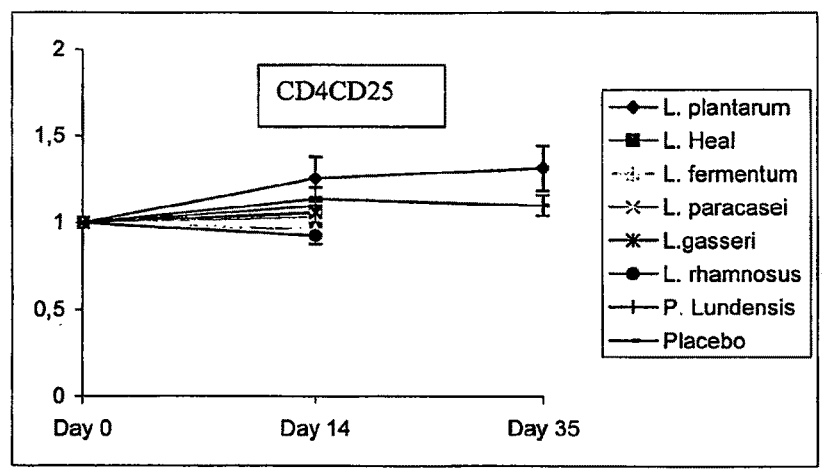
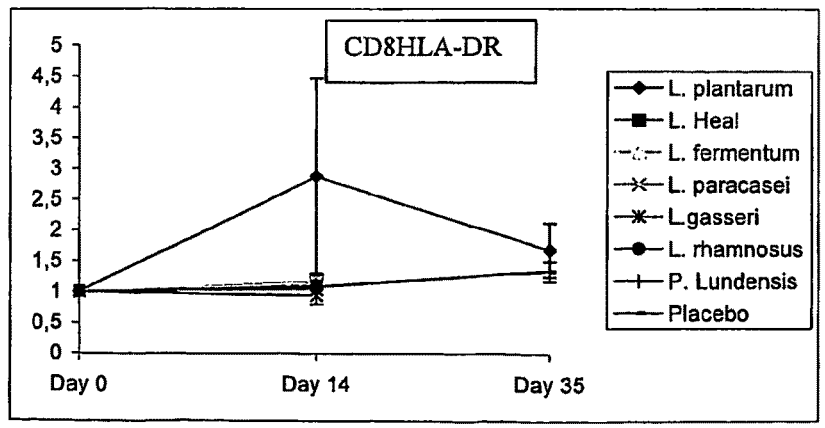

Fig. 5 (continued)
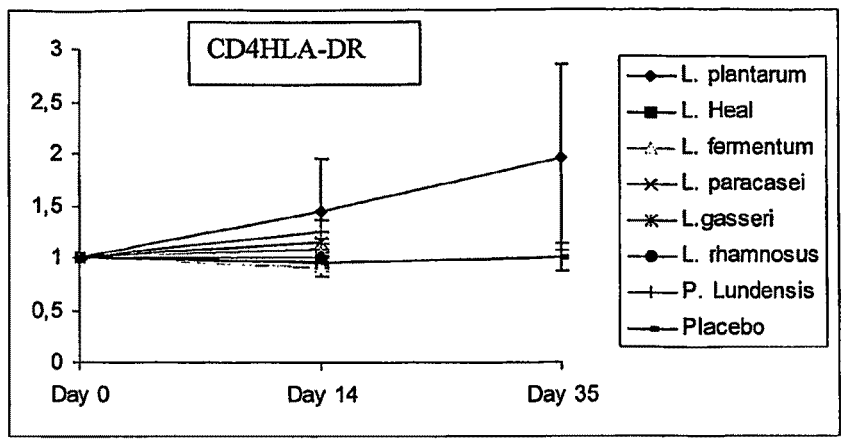
Fig. 6.
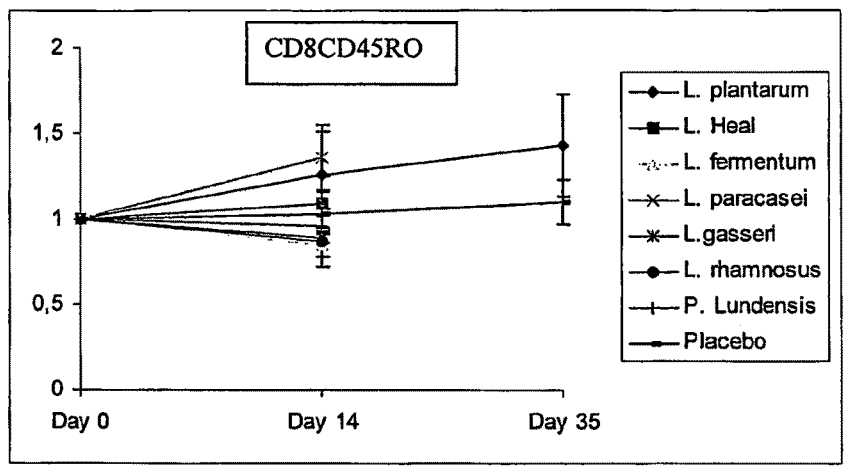
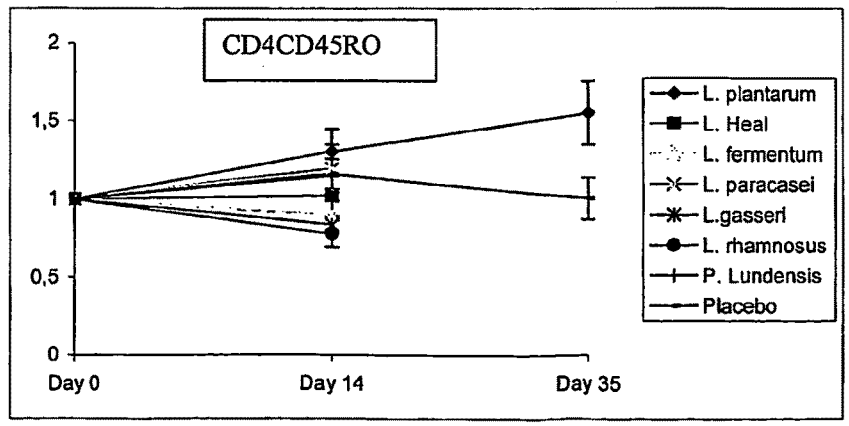

USE OF *LACTOBACILLUS* FOR TREATMENT OF AUTOIMMUNE DISEASES

FIELD OF THE INVENTION

The present invention relates to the use of at least one probiotic bacterial strain selected from *Lactobacillus* for the manufacture of a pharmaceutical composition for the treatment and/or prevention of an autoimmune disease.

BACKGROUND ART

Probiotic bacteria are defined as live microorganisms which when administered in adequate amounts beneficially affect the host. Lactobacilli and bifidobacteria are the most frequently used bacteria in probiotic products. These bacteria are generally safe, as are probiotics based on these organisms. The lack of pathogenicity extends across all age groups and to immunocompromised individuals. Intake of different probiotic bacteria has been shown to have clinical benefits in various physiologic or pathologic situations. The most clear cut effects have been shown in diarrhea caused by antibiotic therapy or rotavirus infection. There are also studies showing positive clinical effects in inflammatory bowel diseases, atopic dermatitis and hypercholesterolemia after intake of probiotic bacteria. The mechanism, by which probiotic bacteria contribute to these clinical improvements are not clear. In vitro human, as well as both in vivo and in vitro animal studies have shown that different species of lactobacilli affects the innate and acquired immune system in many different ways.

Clinical studies have mainly shown stimulation of the innate cellular immune system and enhancement of humoral immune responses to natural infections and systemic or oral immunisation. Regarding effects of the innate immune system, increased phagocytic activity of polymorphonuclear cells (PMN) and increased NK cell tumor killing activity have been reported. To our knowledge, there are no clinical studies showing effects on the specific cellular immune system after intake of probiotic bacteria.

In the present application the effects on the innate and acquired immune system following daily intake of lactobacilli or the Gram-negative bacteria *P. lundensis* have been thoroughly investigated amongst other things. Interestingly, it has been observed an activation of the specific cellular immune system in subjects receiving *L. plantarum* and indications of such in subjects receiving *L. paracasei*. Moreover, immunity-enhancing effects on the innate immune system, such as expansion of the NKT cell population and increased phagocytic activity were observed in subjects receiving different lactobacilli species. Intake of the Gram-negative bacteria *P. lundensis* had no effects, whatsoever, on the different immune parameters measured in this study.

An increasing problem in the west world are the autoimmune and autoimmune related diseases where the immune system of the human individual attacks itself by mistake and the individual can get very sick. The autoimmune diseases can affect connective tissues and many other parts of the body such as specific organs such as the skin, the nerves, the brain, lungs, kidneys and joints. An example of an autoimmune disease in the nerves and the brain is multiple sclerosis and on the skin an example is psoriasis. The autoimmune disease takes many different forms and there are also many treatments for them. The treatment depends on the type of the disease and the organ affected.

There is a need within the art to alleviate and treat the symptoms related to autoimmune diseases as well as provide a prophylactic treatment before the disease has developed. These issues are the subject matter of the present invention that will be apparent from the following.

SUMMARY OF THE INVENTION

An object of the present invention is the use of at least one strain of probiotic bacteria selected from *Lactobacillus* for the manufacture of a pharmaceutical composition for the treatment and/or prevention of an autoimmune disease.

Another object of the present invention is a method for the treatment of an autoimmune disease, wherein at least one strain of probiotic bacteria selected from *Lactobacillus* is administered to an individual.

BRIEF DESCRIPTION OF THE DRAWINGS

FIG. 1 shows the numbers of volunteers reporting any minor adverse gastrointestinal effects during the trial.

FIG. 2 shows base line numbers (day 0) of different lymphocytes per ml blood (mean±(SEM))

FIG. 3 shows base line (day 0) percentages or GMFI (mean±(SEM)) of lymphocytes positive for different cell activation and memory markers.

FIG. 4. Subjects were randomly assigned to nine different study groups. The trial started with a wash out period of two weeks. Thereafter, the active study period followed. During this period, the subjects consumed one dose of study product per day for 14 (*L. plantarum* Heal 19, *L. fermentum*, *L. paracasei*, *L. gasseri*, *L. rhamnosus*, *P. lundensis* groups) or 35 days (*L. plantarum* 299v and placebo group). Each dose contained $10^{10}$ coloni forming units (CFU) (lactobacilli groups) or $10^9$ CFU bacteria (*P. lundensis* group).

FIG. 5. Percentages of lymphocytes expressing the activation phenotypes CD8CD25, CD8HLA-DR, CD4CD25 and CD4HLA-DR was analysed by flowcytometry. Group means (±SEM) based on individual ratios, day 14/day 0 and day 35/day 0 (for *L. plantarum* 299v and placebo group only) is shown.

FIG. 6. Percentages of lymphocytes expressing the memory phenotypes CD8CD45RO and CD4CD45RO was analysed by flowcytometry. Group means (±SEM) based on individual ratios, day 14/day 0 and day 35/day 0 (for *L. plantarum* and placebo group only) is shown.

DETAILED DESCRIPTION OF THE INVENTION

Figure 7:
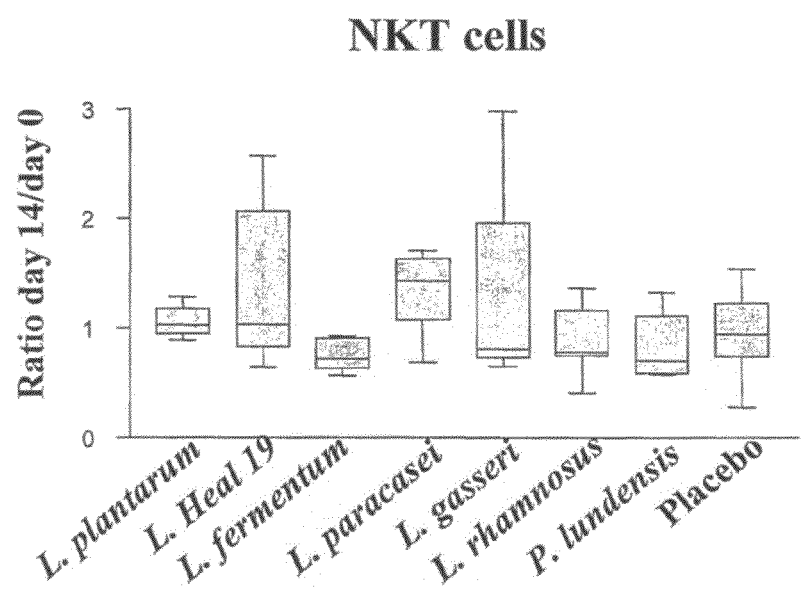
FIG. 7. Percentages of lymphocytes positive for the NKT cell markers (CD56CD16CD3) was analysed by flow-cytometry. Group calculations are based on individual ratios (day 14/day 0).

In an embodiment of the invention the at least one strain of probiotic bacteria selected from *Lactobacillus* is used in the manufacture of a pharmaceutical composition for treatment of an autoimmune disease selected from, but not limited to, an organ specific autoimmunity such as multiple sclerosis (MS), allergy, psoriasis, rhematoid arthritis, Chrohns' disease, ulcerative colitis, type I diabetes mellitus, inflammatory bowl diseases, or systemic lupus.

Any other autoimmune disease, not specifically mentioned here, that the probiotic bacteria have an effect on (preventive or treatable) are also within the scope of the present invention.

In the present context the word "treatment and/or prevention" includes a prophylactic treatment of an individual, i.e. the treatment with the probiotic bacteria is started before the disease has developed in order to prevent the disease, as well as a treatment of a disease that already has developed in an individual. In the latter case an alleviation of the symptoms is for instance expected or the general condition of the patient is enhanced or the patient is cured from the disease. Thus, the individual may be a person at risk for developing an autoimmune disease or not or already be a diseased patient.

The *Lactobacillus* used according to the invention may be selected from, but not limited to, the group consisting of *Lactobacillus plantarum, Lactobacillus rhamnsosus, Lactobacillus fermentum, Lactobacillus paracasei* and *Lactobacillus gasseri*.

Other probiotic bacterial strains, than the ones explicitly disclosed herein, may naturally be used according to the present invention and are within the scope of the invention as long as they provide the desired effects, i.e. have a preventive effect on an autoimmune disease or alleviates the symptoms of an autoimmune disease.

The *Lactobacillus plantarum* used according to the invention may be selected from, but not limited to, the group consisting of *Lactobacillus plantarum* 299, DSM 6595, *Lactobacillus plantarum* 299v, DSM 9843, *Lactobacillus plantarum* HEAL 9, DSM 15312, *Lactobacillus plantarum* HEAL 19, DSM 15313, and *Lactobacillus plantarum* HEAL 99, DSM 15316.

The *Lactobacillus paracasei* used according to the invention may be selected from, but not limited to, the group consisting of *Lactobacillus paracasei* 8700:2, DSM 13434, and *Lactobacillus paracasei* 02A, DSM13432.

The *Lactobacillus gasseri* used according to the invention may be selected from, but not limited to, *Lactobacillus gasseri* VPG44, DSM 16737.

In another embodiment of the invention at least two probiotic strains are used for the treatment and/or prevention of said autoimmune disease. The at least two strains are selected from *Lactobacillus*, preferably from *Lactobacillus plantarum, Lactobacillus rhamnsosus, Lactobacillus fermentum, Lactobacillus paracasei* and *Lactobacillus gasseri*.

In the embodiment where at least two probiotic strains are used for the intended treatment, said at least two strains are intended to be administered sequentially or simultaneously. Thus, the strains may be administered in a mixture in one composition or they may be administered in a sequence separately in different compositions.

In a further embodiment of the invention said pharmaceutical composition is a liquid formulation or a solid formulation, wherein said solid formulation is selected from the group consisting of tablets, sucking tablets, sweets, chewing tablets, chewing gums, capsules, sachets, powders, granules, coated particles and coated tablets, enterocoated tablets and capsules, and melting strips and films, and said liquid formulation is selected from the group consisting of oral solutions, suspensions, emulsions and syrups.

In a yet further embodiment of the invention-said composition comprises a carrier material, wherein said carrier material is independently selected from, but not limited to, the group consisting of oat meal gruel, lactic acid fermented foods, resistant starch, dietary fibres, carbohydrates, proteins, and glycosylated proteins.

In a further embodiment of the invention said pharmaceutical composition is selected from, but not limited to, a medical food, a functional food, a dietary supplement, a nutritional product or a food preparation. Thus, the word "pharmaceutical composition" as used herein does not necessarily mean a pharmaceutical composition in its normal sense such as a medicament, but can also be a product within the field of medical foods, functional foods, dietary supplements, and nutritional products and food products. When being a food product, it may be selected from, but not limited to, beverages, yoghurts, juices, ice creams, breads, biscuits, cereals, health bars, and spreads.

Thus, the use of a composition according to the invention may be very beneficial in the sense of being usable prophylactically, i.e. before the autoimmune disease has developed. Since the pharmaceutical composition used is not necessarily a medicament in its normal sense, but can also be a dietary supplement or functional food, it is very convenient for a normal healthy individual to take to composition of the invention prophylactically.

In an embodiment of the invention each of said strain(s) is present in the composition in an amount of about $1 \times 10^6$ to about $1 \times 10^{14}$ CFU, preferably from about $1 \times 10^8$ to about $1 \times 10^{12}$, and more preferably from about $1 \times 10^9$ to about $1 \times 10^{11}$.

The pharmaceutical composition according to the invention may also comprise other substances, such as an inert vehicle, or pharmaceutical acceptable adjuvants, carriers, preservatives etc., which all are well known to persons skilled in the art.

EXAMPLES

Example 1

Subjects and Trial Criteria

Fifty-seven apparently healthy volunteers within the age range 18-55 years (median, 26 years) were selected for this blind placebo controlled study. Subjects were randomly assigned to eight groups, receiving either one of the following Gram-positive bacteria, *L. plantarum* 299v (n=7), *L. plantarum* Heal 19 (n=7), *L. fermentum* 35D (n=7), *L. paracasei* 8700:2 (n=7), *L. gasseri* VPG44 (n=7), *L. rhamnosus* 271

(n=7), or the Gram-negative bacteria, *P. lundensis* (n=7) or placebo (n=10). The dose of bacteria was $10^{10}$ bacteria/day for lactobacilli and $10^9$ bacteria/day for *P. lundensis*. The control group took skim milk powder (1 g). Depending on the group, the study had a duration period of 6 or 9 weeks consisting of two weeks wash out period, 2 (see FIG. 4A) or 5 (see FIG. 4B) weeks active study period and 2 weeks follow up period. Each subject was supplied with a list of products containing probiotic products, which should not be consumed during the whole study period. Peripheral blood samples were withdrawn from subjects by venipuncture at two or three time points, day 0, day 14 and day 35. A diary, in which each subject stated adverse effects, health conditions and confirmed intake of study product, was kept during the trial.

Flow Cytometry

Phenotypic analysis of lymphocytes in whole blood was performed by flow cytometry. The following anti-human monoclonal antibodies were used as surface markers for different cell populations: CD3 FITC (SK7), CD4 APC (SK3), CD8 PerCP (SK1), CD19 PerCP (SJ25C1), CD56 PE (MY31), CD16 PE (B73.1), and CD5 FITC (L17F12). Following anti-human monoclonal antibodies were used for detection of different activation and memory markers: CD25 FITC (2A3), HLA-DR PE (L243), CD45RO PE (UCHL-1), CD38 PE (HB7), CD27 PE (L128), and CD11b PE (D12). All antibodies were purchased from Becton-Dickinson (Erembodegum, Belgium). Whole blood (100 µl) was incubated with antibodies (10 µl/antibody) for 30 min at 4° C. in the dark. Thereafter, 2 ml of FACS lysing solution (Becton-Dickinson) was added and incubated for 15 min at 20° C. in the dark. Cells were washed by adding 3 ml FACSFlow and centrifuged at 300×g for 5 min. Washed cells were resuspended in 200 µl FACSFlow and analysed on a FacsCalibur (Becton-Dickinson) with CellQuest software.

Phagocytosis Assay

The phagocytic activity of granulocytes and monocytes were quantified with PHAGOTEST® (Orpegen Pharma, Heidelberg, Germany) according to manufacturers instruction with some modifications. Briefly, $20 \times 10^6$ FITC labeled *E. coli* or FITC labeled *S. aureus* was added to pre-cooled whole blood (100 µl). Blood cells and bacteria were incubated on 37° C. for 10 FacsCalibur with CellQuest software.

Calculations

Individual changes regarding different immune parameters were determined by calculating the ratio between the individual values obtained at day 14 and day 0, or the values at day 35 and day 0. These ratios were used for all group calculations and statistics.

Statistics

All statistical analyses were performed using Statview. Mann-Whitney U test were used to compare different groups.

Results

Clinical Observations

Fifty-four out of fifty-seven volunteers completed the study. Two persons were excluded due to infection and antibiotic treatment (one in the placebo group and one in the group receiving *P. lundensis*). One person was excluded day 16 due to pregnancy (placebo group). Only mild adverse gastrointestinal side effects were reported following intake of study products (FIG. 1).

Intake of Lactobacilli Activates T Cells

There were great baseline (day 0) individual variations regarding activation markers on $CD4^+$ and $CD8^+$ T cells. The baseline percentages of cells expressing different cell surface markers are shown in FIG. 2. No significant differences were observed between different groups at this time point. Since huge inter-individual variations were observed, it was chosen to compare ratio values at day 14 and day 35 compared to day 0 for each individual. All calculations and comparisons were done on these ratio values (day 14/day 0 and day 35/day 0). After 14 days of intake of study product containing *L. plantarum* 299v there was an approximately twofold increase of the expression of the activation marker CD25 on $CD8^+$ T cells (p=0.01) (FIG. 5). There was also a strong, although not significant (p=0.12), indication of upregulation of HLA-DR on $CD8^+$ cells following *L. plantarum* 299v intake. In addition, it was also observed a tendency towards activation of $CD4^+$ T cells after *L. plantarum* 299v intake. Intake of the other lactobacilli species included in this study, as well as the Gram-negative bacteria *P. lundensis* activated neither $CD8^+$ nor $CD4^+$ T cells. However, there was a tendency that intake of *L. paracasei* did increase the expression of HLA-DR on $CD4^+$ T cells (p=0.18).

Intake of Lactobacilli Induces a Memory Phenotype of CD4+ T Cells

Geometric means of the fluorescence intensity (GMFI) of the expression of CD45RO on CD4+ and CD8+ T cells were compared between groups receiving different study products. As above, group calculations based on individual ratio values (day 14/day 0 and day 35/day 0) were used for comparisons. After 35 days of intake of study product containing *L. plantarum* 299v the CD45RO GMFI on CD4+ T cells increased significantly (p=0.03). There was also a tendency towards increased CD45RO expression on CD8+ T cells following intake of *L. plantarum* (FIG. 6). Moreover, intake of *L. paracasei* seems to have a positive effect on upregulation of CD45RO on CD8+ T cells (p=0.10) (FIG. 6).

Effect on Different Cell Populations Following Intake of Study Product

Following intake of *L. pararcasei* there was an increase in the percentage of lymphocytes being identified as NKT cells (P=0.06) (FIG. 7). Relative increase/decrease compared to day 0 could not be detected regarding other cell populations, such as CD4+ T cells, CD8+ T cells, B cells, B-1 cells (CD19+CD5+), NK cells, granulocytes and monocytes.

Phagocytic Activity

Figure 8:
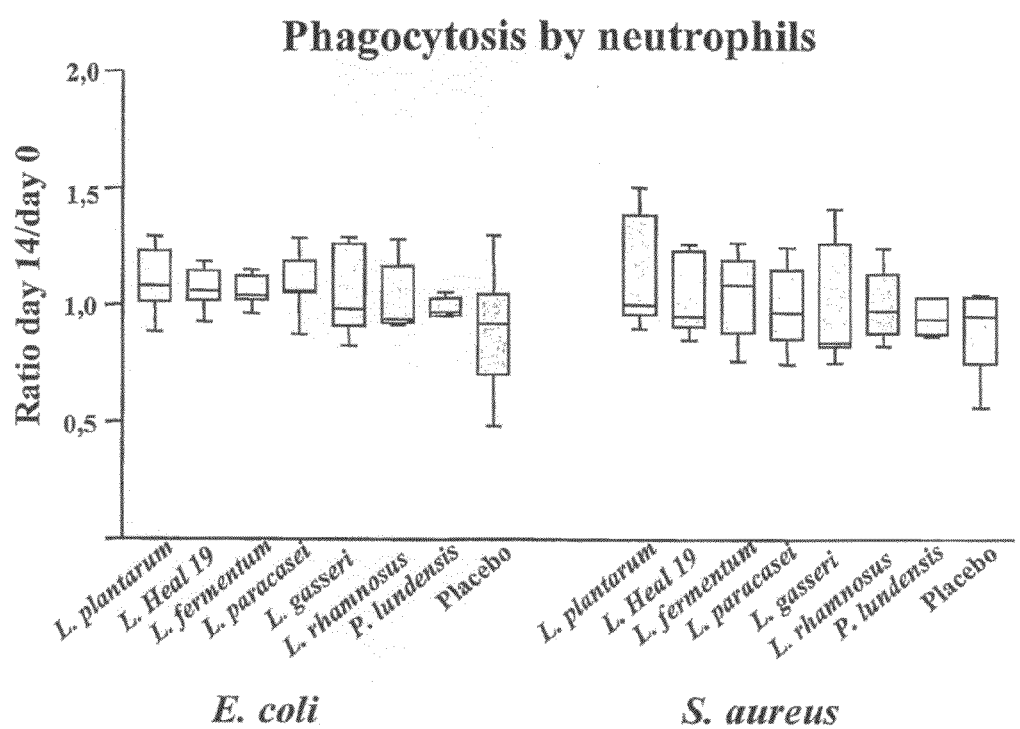
FIG. 8. The phagocytic activity of neutrophils was analysed by incubating whole blood cells with FITC-labelled *E. coli* or *S. aureus*. The ratio between mean fluorescence values obtained at day 14 and day 0 was determined individually and group calculations are shown in this figure.

Granulocytes and monocytes were identified in the FSC-SSC diagram. The ability of these cells to phagocytose FITC-labelled Gram-positive or Gram-negative bacteria was tested. As shown in FIG. 8, granulocytes from volunteers given *L. plantarum* 299v (p=0.064), *L. plantarum* Heal 19 (p=0.064), *L. fermentum* (p=0.064) or *L. paracasei* (p=0.05) were more efficient then granulocytes from placebo treated volunteers in phagocytosis of the Gram-negative bacteria *E. coli*. However, there was no difference between the groups in phagocytosis of the Gram-positive bacteria *S. aureus*. No differences in the phagocytic activity of monocytes could be detected (data not shown).

Discussion

The primary task of the immune system is to react rapidly and violently to micro-organisms thereby preventing and curing infections. The killing of microorganisms employs powerful mechanisms that also cause harm to our own tissues. Therefore, it is necessary that it neither reacts to our own tissues, nor to innocuous substances present in the environment. Therefore, the immune system develops and maintains tolerance both to the components of our own body, and to food and inhaled proteins. If this fails, a number of diseases may arise. Means to develop specific immune tolerance are an essential task of the immune system.

A central role in all immune reactions is played by the T helper cell. When a T helper cell becomes activated by its specific antigen, it becomes activated, divides, matures and produces a range of cytokines which direct the action of other types of cells in the immune system, such as cytotoxic T cells and B cells. Activation of T helper cells is necessary in order to produce most types of immune reactions, including production of antibodies. Conversely, if activation of T helper cells is prevented, most types of immune reactions are paralysed.

There are several mechanisms by which activation of T helper cells and maintenance of tolerance is ensured. One mechanism is elimination in the thymus of T cells with capacity to recognize and react to own tissue. However, this elimination is not complete and, furthermore, we also need to develop specific immune tolerance to exogenous antigens. Otherwise we would react violently to all types of inhaled and ingested substances, leading to massive inflammation and wasted immune resources.

A cell type that is central for maintenance of tolerance is the regulatory T cell. This cell type can be recognized by certain markers, such as surface expression of CD4 and CD25, possession of intracellular CTLA-4, and transcription of the nuclear protein Foxp3. The regulatory T cells are capable of preventing other T cells to become activated when encountering harmless substances and, hence, prevent all types of unwanted immune reactions.

In the present context the symbol "+" in connection with a certain marker such as CD4+ and CD25+ means that the marker is expressed on a T cell. For instance CD4+CD25+ T cells are T cells that express both the CD4 marker and CD25 marker on its surface. However, nothing is said about the amount of the marker that is expressed, only that it is present. In the present context the symbol "++" in connection with a marker such as CD4++ or CD25++ means that there is a lot of marker expressed. The regulatory T cells are those cells with a lot of CD25 on the surface, i.e. CD4+CD25++ cells. On the other hand, CD4+CD25+ T cells are only activated T cells. Sometimes the specific symbols "+" and "++" are not used, e.g. CD4CD25 only, and this means that the cells are activated such CD4+CD25+ cells. Thus, CD4CD25 is the same as CD4+CD25+. When discussing regulatory T cells, it is always written as CD4+CD25++ cells.

This blind placebo-controlled study is unique in that it is the first study comparing the influence of several immune parameters following intake of different Gram-positive lactobacilli or the Gram-negative bacteria *P. lundensis*. Interestingly, intake of *P. lundensis* did not influence any of the measured parameters. In contrast, intake of lactobacilli affected different components of both the specific and innate immune system. A novel finding in this study was that intake of *L. plantarum* had a pronounced positive effect on activation and induction of memory cells in the T cell populations. There was a significant upregulation of the IL-2 receptor α chain (CD25) and a strong tendency towards upregulation of HLA-DR on cytotoxic T cells. A tendency towards up-regulation of these activation markers was also observed on helper T cells after intake of *L. plantarum*. Expression of activation markers indicates that the T cells have started to proliferate in response to antigen-specific or non-specific stimuli and that these cells more readily exert their effector functions compared to resting T cells. The mechanisms behind *L. plantarum* induced activation of T cells could be via antigen presenting cells that are activated by toll-like receptors binding to microbial compounds. Activation of antigen presenting cells makes them more efficient in presenting antigen to T cells. In addition, both helper and cytotoxic T cells have shown to have various expressions of toll-like receptors, which probably make these cells sensible for non-specific activation by microbial components and products.

In analogy to the helper T cell compartment, expression of CD45RO seems to mark a memory population also among cytotoxic T cells. There was found a significant increase in the expression of this memory cell marker on helper T cells, and a tendency towards upregulation on cytotoxic T cells following 35 days intake of *L. plantarum*. In addition, intake of *L. paracasei* also showed a tendency towards upregulation of CD45RO on cytotoxic T cells. Relative to naive T cells, CD45RO+ T cells can secrete a broad spectrum of cytokines. Moreover, CD45RO+ T cells can proliferate and produce IL-2 when the CD3-TCR complex is stimulated under suboptimal conditions, whereas naïve T cells require a strong CD3-TCR stimulus to carry out these functions. The formation of memory T cells is important for induction of an efficient immune response after infection and vaccination.

The innate cellular immune system was also affected by intake of probiotic bacteria. It was demonstrated that the natural killer T (NKT) cell population was expanded following intake of *L. paracasei*. NKT cells constitute a lymphocyte subpopulation that coexpress the NK cell marker CD56 and the T cell marker CD3-T cell receptor complex. Studies in both humans and mice. have demonstrated that NKT cells play a central role in the regulation of autoimmune diseases, such as multiple sclerosis, type I diabetes, and systemic lupus. NKT cells also exert effector functions against tumour and virus infected cells. Thus, NKT cells are pleotropic in their functions. Other clinical studies evaluating the immunological effects of probiotic bacteria have shown that intake of *L. rhamnosus* HN001 and *Bifidobacterium lactis* HN019 enhance NK (including NKT) cell tumour killing activity of K562 cells. In this study it was also confirmed that phagocytic activity of polymorphonuclear cells is increased after intake of different lactobacilli. The consequence of the observed effects on the different immune parameters in the present study is that one could speculate that the coincident activation of cytotoxic T cells and NKT cell expansion points to a strengthened immune defense against viral infections and/or tumours. The in vitro finding that lactobacilli induce mononuclear cells to secrete IL-12 and IL-18, supports the theory that intake of these bacteria stimulates cell-mediated activity.

In accordance with the present invention it has been concluded that intake of *L. plantarum* and *L. paracasei* has a profound effect on the specific and innate cellular immune system.

Example 2

The goal of this example was to investigate the effect on the immune system by giving the same species of lactobacilli for a longer period of time compared to several lactobacilli (different species) administered in a sequence one after the other.

The volunteers were given a powder with freeze-dried bacteria during 14 or 35 days. As gram-positive bacteria the probiotic bacteria *Lactobacillus plantarum* 299v is used alone or in combination with *L. rhamnosus, L. fermentum, L. paracasei*, and *L. gasseri*. As gram-negative bacteria *Pseudomonas lundensis* is given.

The following groups are studied:
1) *Lactobacillus plantarum* 299v 35 days
2) *L. plantarum* 299v 7d, *L. rhamnosus* 271 7d, *L. fermentum* 35D 7d, *L paracasei* 8700:2 7d, *L. gasseri* VPG44 7d. Totally 35 days. (Sequence)
3) A mixture of *L. plantarum* 299v, *L. rhamnosus* 271, *L. fermentum* 351D, *L. paracasei* 8700:2, *L. gasseri* VPG44. Totally 14 days
4) *L. rhamnosus* 271, 14 days
5) *L. fermentum* 35D, 14 days 6) *L. paracasei* 8700:2, 14 days
7) *L. gasseri* VPG44, 14 days
8) *Pseudomonas lundensis*, 14 days
Control group 1) Placebo, 35 days
Control group 2) Placebo, 14 days Blood samples are taken at day 0, 14 and 35. The amount of helper T cells (CD4+) expressing high amounts of CD25 was defined in each group by flow cytometry, as have been specified above in experiment 1.

Results

On day 14, there was a borderline significance of CD4+ CD25++ T cells being expanded in individuals consuming the sequence of five different lactobacilli strains.

Discussion

T helper cells (CD4+) expressing high density of the CD25 molecule (CD4+CD25++) have in other studies been shown to be important in order to protect against autoimmune diseases, allergies and inflammatory bowel diseases. The finding that these cells are expanded after intake of a sequence of different lactobacilli indicate that intake of these bacteria might be beneficial for the individual concerning the risk of developing the above mentioned diseases.

Example 3

Animals

Eight-week-old C57BL/6 mice were purchased from Taconic Europe (Denmark). Animals were kept and bred at the conventional animal facility of department of cell and organism biology, Lund University, and all experiments were performed in accordance with the ethical committee in Malmö-Lund, Sweden. The mice were fed normal diet and water ad libitum, and were allowed an acclimatization period to the new environment for at least one week before the experiments were started. The mice used in the EAE experiments were weighed, examined for clinical signs of EAE, and scored according to the scale described in clinical evaluation every day throughout the experiment. Mice that were scored 6 were supplemented once a day with 0.5 ml of physiologic saline solution subcutaneously to avoid dehydration. Food was placed on the cage floor when any mouse showed signs of clinical disease. Mice that scored 7 were sacrificed for ethical reasons. The experiments were ended 24 days post immunization.

Antigens

An encephalogenic peptide from myelin oligodendrocyte glycoprotein (MOG) was used to induce EAE (experimental autoimmune encephalomyelitis) in mice. The synthetic peptide, amino acids 35-55 (MEVGWYRSPFSRVVH-LYRNGK) (SEQ ID NO:1), was purchased from Schafer-N, Copenhagen, Denmark. The peptide used was 99% pure.

Immunization

EAE was induced as earlier described in female C57BL/6 mice. Briefly, each animal was immunized under isoflurane anaesthesia by a s.c. injection in the flank with 100 µl of a 1:1 emulsion of 200 µg of $MOG_{35-55}$ in PBS and CFA containing *Mycobacterium tuberculosis* H37Ra (Difco, Detroit, Mich.). Immediately thereafter and 48 h after immunization, the mice were given an intraperitoneal injection of 0.1 ml of 4 µg/ml pertussis toxin (Sigma).

Clinical Evaluation

Clinical signs of EAE were scored according to a scale from 0 to 8 as follows: 0, no signs of clinical disease; 1, weakness in the tail; 2, paralysed tail; 3, hind limb paresis and gait disturbance; 4, paralysis of one hind limb; 5, total hind limb paralysis with hind body paresis, the mouse is active and moves around using its forelimbs; 6, total hind limb paralysis with hind body paresis and severely impaired mobility; 7, quadriplegia, no mobility, moribund state; 8, dead.

Bacterial Strains and Treatment

*L. plantarum* HEAL 9 and *L. paracasei* 8700:2 were provided by Probi AB (Ideon, Lund, Sweden). The bacteria were harvested by centrifugation, washed once, and resuspended in tap water to a final concentration of $2 \times 10^9$ colony-forming units (CFU)/100 ml in a bottle. A third bottle was prepared with a mixture of both *L. plantarum* HEAL 9 and *L. paracasei* 8700:2 to a final concentration of $2 \times 10^9$ CFU/100 ml. The bottles have been washed and vehicles including the bacteria were prepared every day. The experiments were conducted with ten mice in each treatment group. Each animal drank 4-5 ml vehicle/day including approximately $10^8$ CFU. Control animals received tap water.

Results

Probiotic Treatment Suppressed Development of MOG Induced EAE

Figure 9:
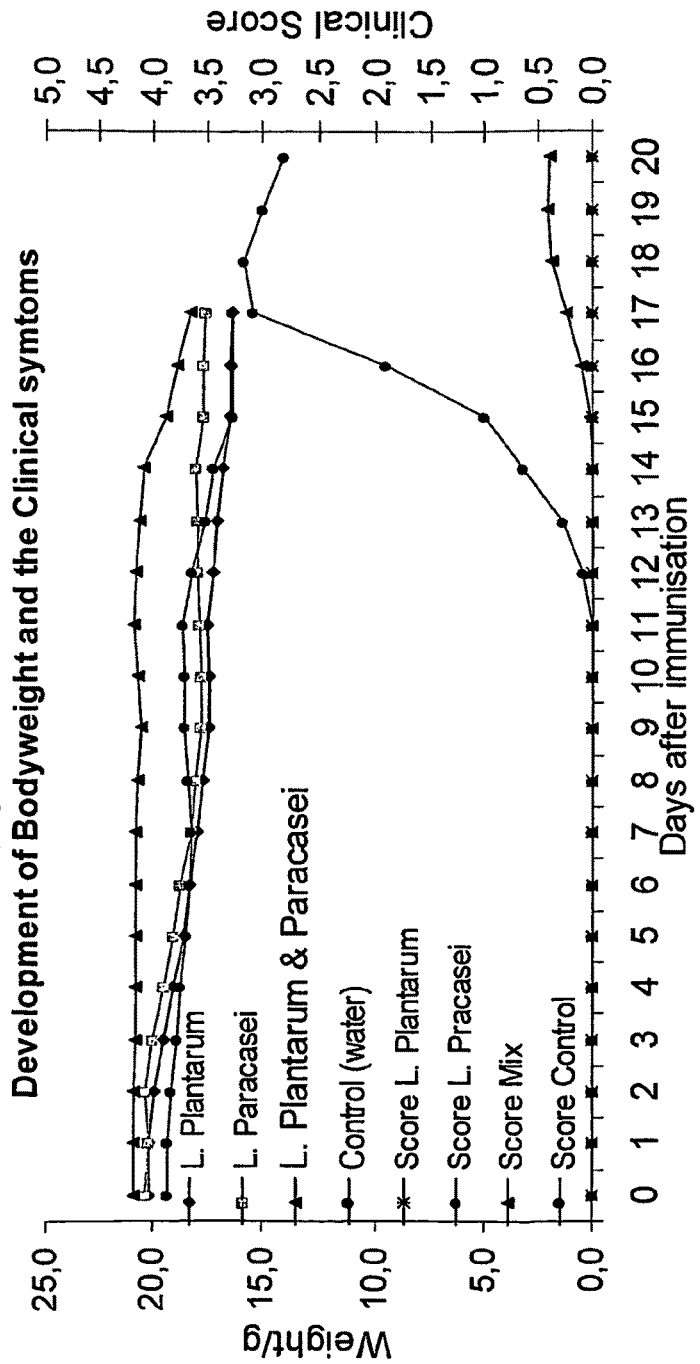
FIG. 9. shows prophylactic treatment of EAE development, bodyweight and the clinical symptoms (experiment 3).
Figure 10:
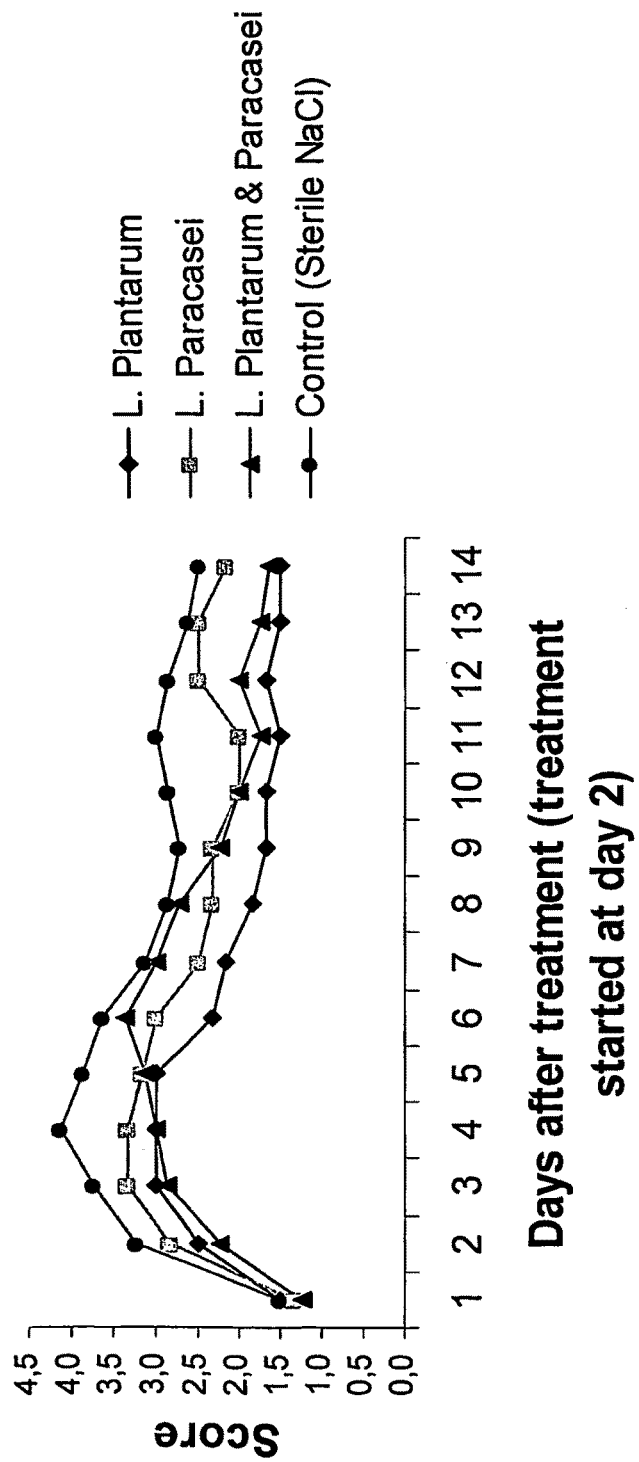
FIG. 10. shows therapeutic treatment of chronic inflammation in EAE treatment started on day post onset (experiment 3).

In order to study the anti inflammatory effect of probiotics, three groups of animals were pre-treated with probiotics, *L. plantarum* HEAL 9, *L. paracasei* 8700:2 and a mixture of *L. plantarum* HEAL 9 and *L. paracasei* 8700:2, in twelve days and immunized for EAE with an emulsion of CFA and $MOG_{35-55}$ at day 0. Animals were then treated throughout the whole experiment (until day 24). A fourth group of animals received only tap water as control. As shown in FIG. 10 treatment with *L. plantarum* HEAL 9 or *L. paracasei* 8700:2 successfully prevented the development of chronic EAE for 10 days compared to the control mice that showed a severe EAE with start at day 11. Mice treated with a mixture of bacteria also showed a delay on onset for about five days compared to the control. These mice developed a more severe EAE compared to the mice treated with single bacteria. At day 24, the incidence of diseased animals was significantly reduced, 14% in animals treated with single bacteria, compared to the 91% in control mice. The incidence for animals receiving a mixture of bacteria was 60%. When analysing the changes in the weight of the animals during the experiment, it has surprisingly been shown that treatment with a mixture of two bacteria inhibited a decrease of weight which usually occur before the onset of the disease (FIG. 9). The animals treated with single bacteria were decreased in weight as control mice despite showing no signs of paralysis.

Prophylactic Treatment of EAE

Animals were treated with probiotics 12 days before immunisation and throughout the experiment.

100 ml drinking water including different bacteria was freshly prepared every day.

Approximately 1.108 bacteria/mouse/day. Control mice received only water.

$N_{Plantarum}=7$, $N_{Paracasei}=7$, $N_{Mix}=10$, $N_{Control}=11$

The results are shown in FIG. 9.

Therapeutic Treatment of Chronic Inflammation in EAE

Oral treatment with Probiotics one day after onset of EAE. Animals were treated individually by a feeding needle.

Approx. 1.108 bacteria/mouse/day. Control mice received sterile NaCl 9 mg/ml.

$N_{Plantarum}=6$, $N_{Paracasei}=6$, $N_{Mix}=8$, $N_{Control}=8$

The results are shown in FIG. 10.

Experiment 4

Suppression of Chronic Inflammation in Central Nervous System by Oral Administration of *Lactobacillus paracasei* and *Lactobacillus plantarum*

The aim of this study was to examine whether probiotics could affect T cell-mediated chronic inflammation in central nervous system. We hypothesized that oral treatment of probiotics exerts an anti-inflammatory effect by immune modulation of pathogenic T cell effectors.

Material and Methods

Animal Model

Experimental Autoimmune Encephalomyelitis (EAE), an animal disease model of multiple sclerosis, will be induced by immunisation with, myelin oligodendrocyte glycoprotein (MOG) peptide 35-55, in Complete Freund's Adjuvant. Pertussis toxin is also injected in connection to the immunization to further enhance inflammatory responses. The animals start to show the clinical symptoms after two weeks. The signs of EAE are scored into eight categories: 0—, no signs of clinical disease; 1—weakness in the tail; 2—paralyzed tail; 3—paresis and gait disturbance; 4—paralysis of one limb; 5—paralysis of two limbs; 6—two limbs paralyzed and paresis of a third limb, the mouse still able to move forward; 7—quadriplegia, no mobility and moribund state; 8—dead.

Probiotic Bacterial Strains

*Lactobacillus paracasei* 8700:2, *Lactobacillus paracasei* defacti, *Lactobacillus plantarum* Heal 9, *Lactobacillus plantarum* Heal 19, *Lactobacillus plantarum* 299v and *Lactobacillus delbrueckii* were provided by Probi AB.

Treatment Protocols

Prophylactic treatment; 100 ml drinking water including $1.10^9$-$1.10^{10}$ different bacteria was freshly prepared every day. Each mouse drinks approx 5 ml≈$1.10^8$-$1.10^9$ bacteria/mouse/day. Animals were treated in 7-14 days prior to the immunisation and throughout the whole experiment. Control mice received only water. In our recent experiment, animals are treated with feeding needles 10 days after the immunisation, every second day throughout the experiment.

Therapeutic treatment; Ten days after the onset, each animal received $1.10^9$ bacteria by individual treatment with feeding needles, every second day throughout the experiment. Control mice received saline.

Methetraxate (MTX); MTX were administered i.p. in a final concentration of 2.5 mg/kg, every second day throughout the experiment.

Analysis

Different organs and materials were isolated from the animals for further investigations; Brain, spinal cord, spleen, lymph nodes (mesenteric, inguinal), intestine (regions including Peyer's Patches) and blood. Some organs have been treated with isopentan for immunohistochemistry analysis. Some spleen and lymph node cells were analysed by flow cytometri (FACS) or put in the cultures and stimulated with MOG peptide, anti CD3 and LPS for further cytokine investigations by ELISA.

Results

Prophylactic Treatment

Animals were treated with $1.10^8$ *Lactobacillus paracasei* 8700:2 or *Lactobacillus plantarum* Heal 19 for seven days before immunisation. EAE was suppressed significantly for a short period of time.

Figure 11:
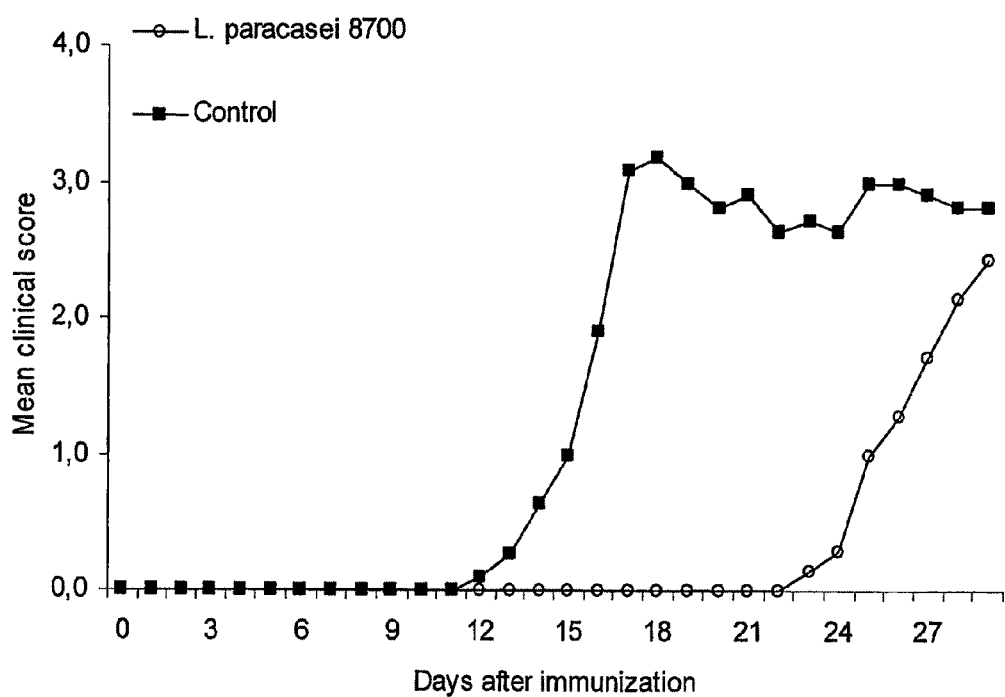
FIGS. 11 and 12. shows the delay of the onset of EAE by giving *L. paracasei* 8700:2 or *L. plantarum* HEAL 9 compared to control.
Figure 12:
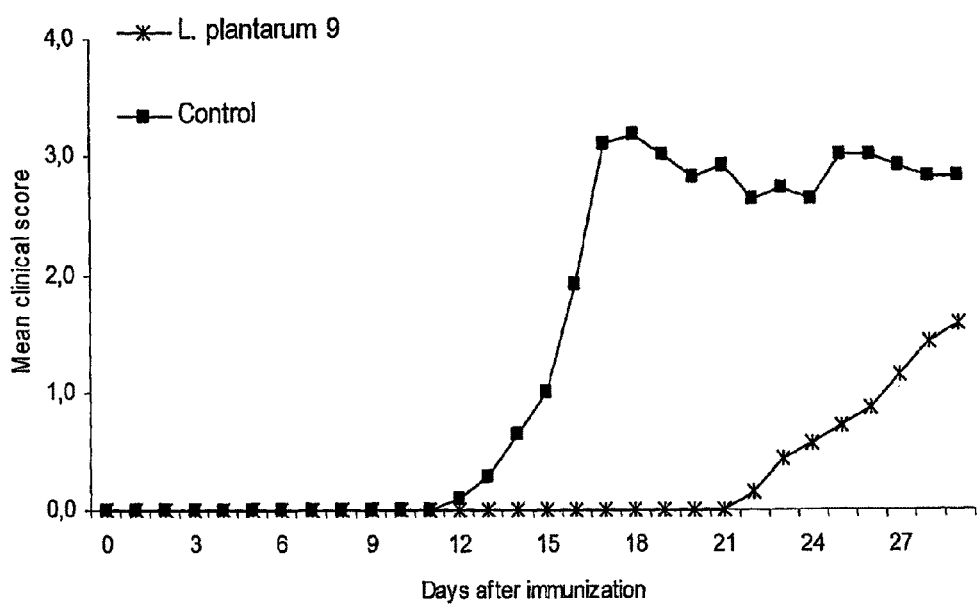

Animals were treated with $1.10^9$ *Lactobacillus paracasei* 8700:2 or *Lactobacillus plantarum* Heal 9 for twelve days before immunisation. The onset of EAE was delayed for more than one week and resulted to a milder development of EAE (See FIGS. 11 and 12).

Immunohistochemical analysis of spinal cord showed significantly lower amounts of the inflammatory T cells in probiotic treated animals. Proliferation assay of splenocytes in vitro revealed equal MOG specific proliferation of T cells but interestingly they produced significantly lower amounts of inflammatory cytokines TNF-α and IFN-γ and higher amounts of IL-4 and IL-10.

*Paracasei* treated animals showed higher levels of total IgG and IgA antibodies in the plasma. FACS analysis of the mesenteric lymph nodes showed an increase of $CD4^+CD25^+$ T cells. Immunohistochemical analysis of the spleen showed an increase of $Foxp3^+$ ($T_{reg}$) cells.

Screening 1;

Five different lactobacilli (*Lactobacillus paracasei* 8700:2, *Lactobacillus paracasei* defacti, *Lactobacillus plantarum* Heal 9, *Lactobacillus plantarum* Heal 19 and *Lactobacillus plantarum* 299v) have been screened for suppression of EAE by a prophylactic treatment protocol. Best suppression was achieved by using *Lactobacillus paracasei* 8700:2, *Lactobacillus plantarum* Heal 9, and *Lactobacillus plantarum* 299v.

Figure 13:
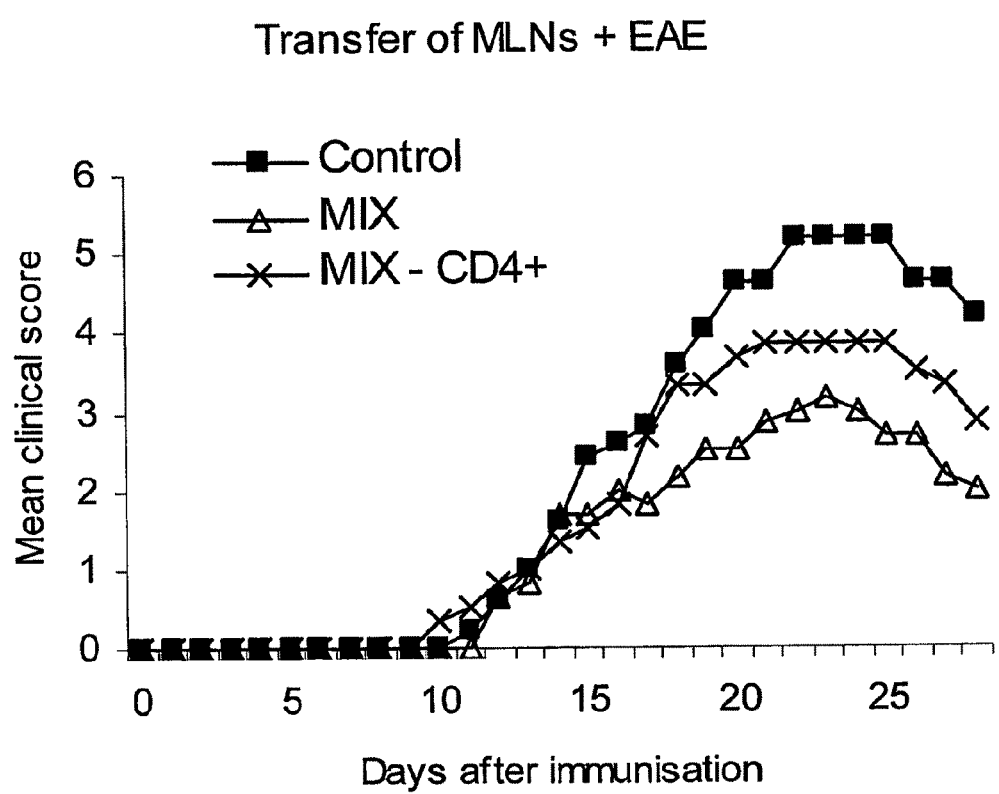
FIG. 13 shows that EAE was suppressed by a mixture of probiotic strains *L. paracasei* 8700:2, *L. plantarum* HEAL 9, and *L. plantarum* HEAL 19. It further shows that the suppression effect was disrupted by removing CD4+ T cells.

Transfer 1;

Animals were treated with *Lactobacillus paracasei* 8700:2, *Lactobacillus plantarum* Heal 9, or a mixture of both strains, for two weeks. Mesenteric lymph node cells were then collected and transferred to recipients (i.v.) that were immunised for EAE one-day post transfer. EAE was significantly suppressed by cells from animals treated with a mixture of two strains. The suppression effect was disrupted by removing CD4+ T cells. (see FIG. 13).

This experiment was repeated again including a group of animals treated with a mixture of tree strains including *Lactobacillus paracasei* 8700:2, *Lactobacillus plantarum* Heal 9 and *Lactobacillus plantarum* Heal 19.

Animals were immunised for EAE. 10 days after the onset of EAE, they were individually treated with a mixture of Lactobacillus paracasei 8700:2, *Lactobacillus plantarum* Heal 9 and *Lactobacillus plantarum* Heal 19. Established disease of EAE was significantly suppressed compare to the control receiving saline. This experiment has successfully been repeated with similar result. Treatment with unspecific bacteria *Lactobacillus pelbrueckii* or Methetraxate (as a general anti inflammatory drug) were ineffective showing the unique therapeutic effect of this protocol.

Figure 14:
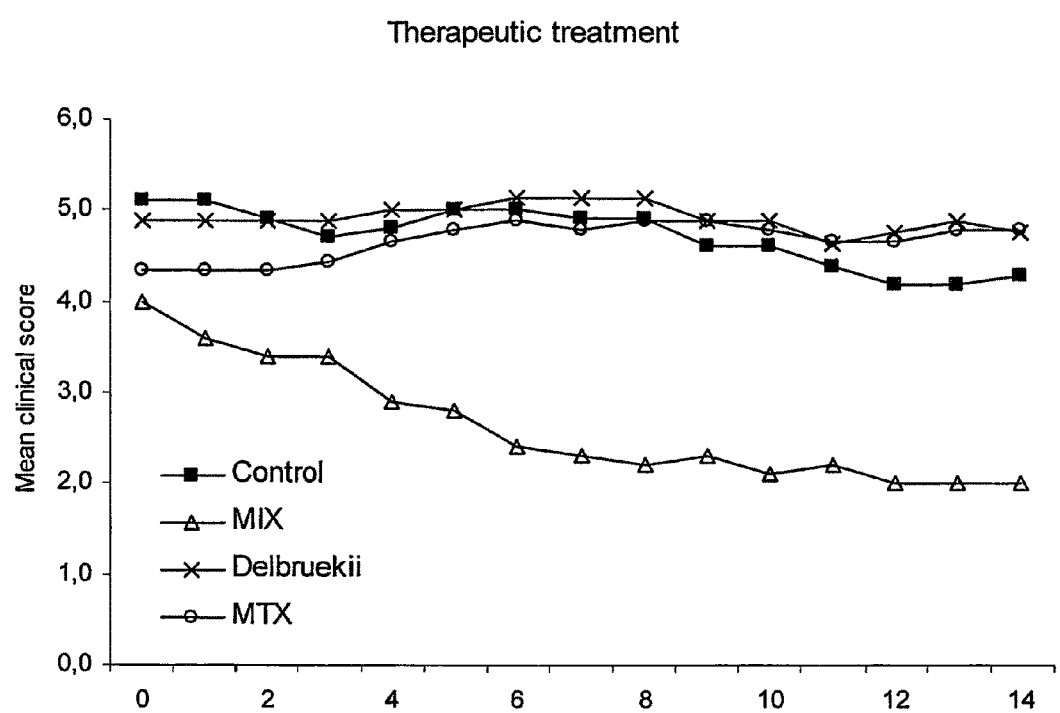
FIG. 14. shows that EAE was suppressed by a mixture of *L. paracasei* 8700:2, *L. plantarum* HEAL 9, and *L. plantarum* HEAL 19 compared to control, methetraxate and *L. delbrueckii*.
Figure 15:
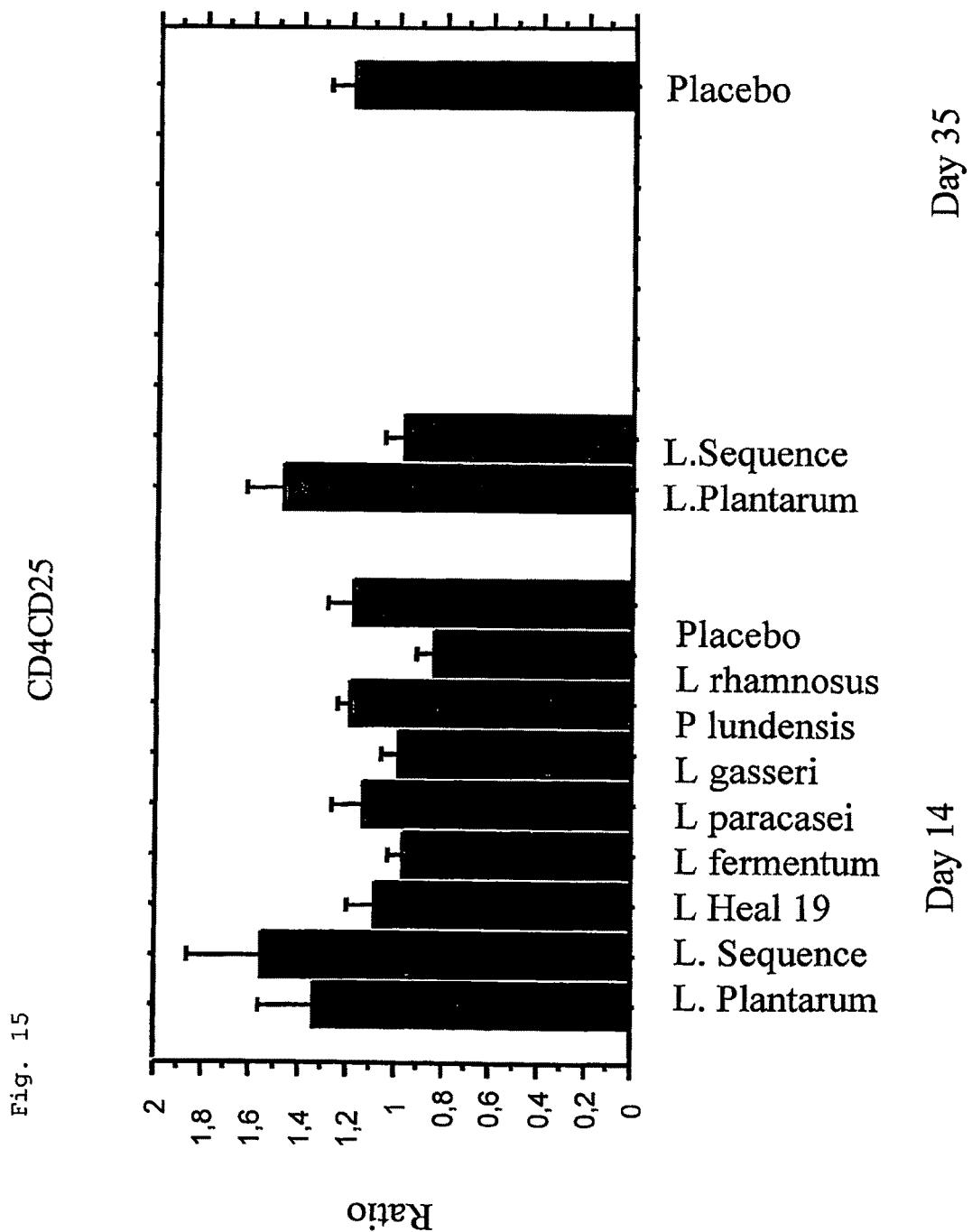
FIG. 15 shows the ratio of lymphocytes expressing the activation phenotypes CD4CD25 from experiment 2.
Figure 16:
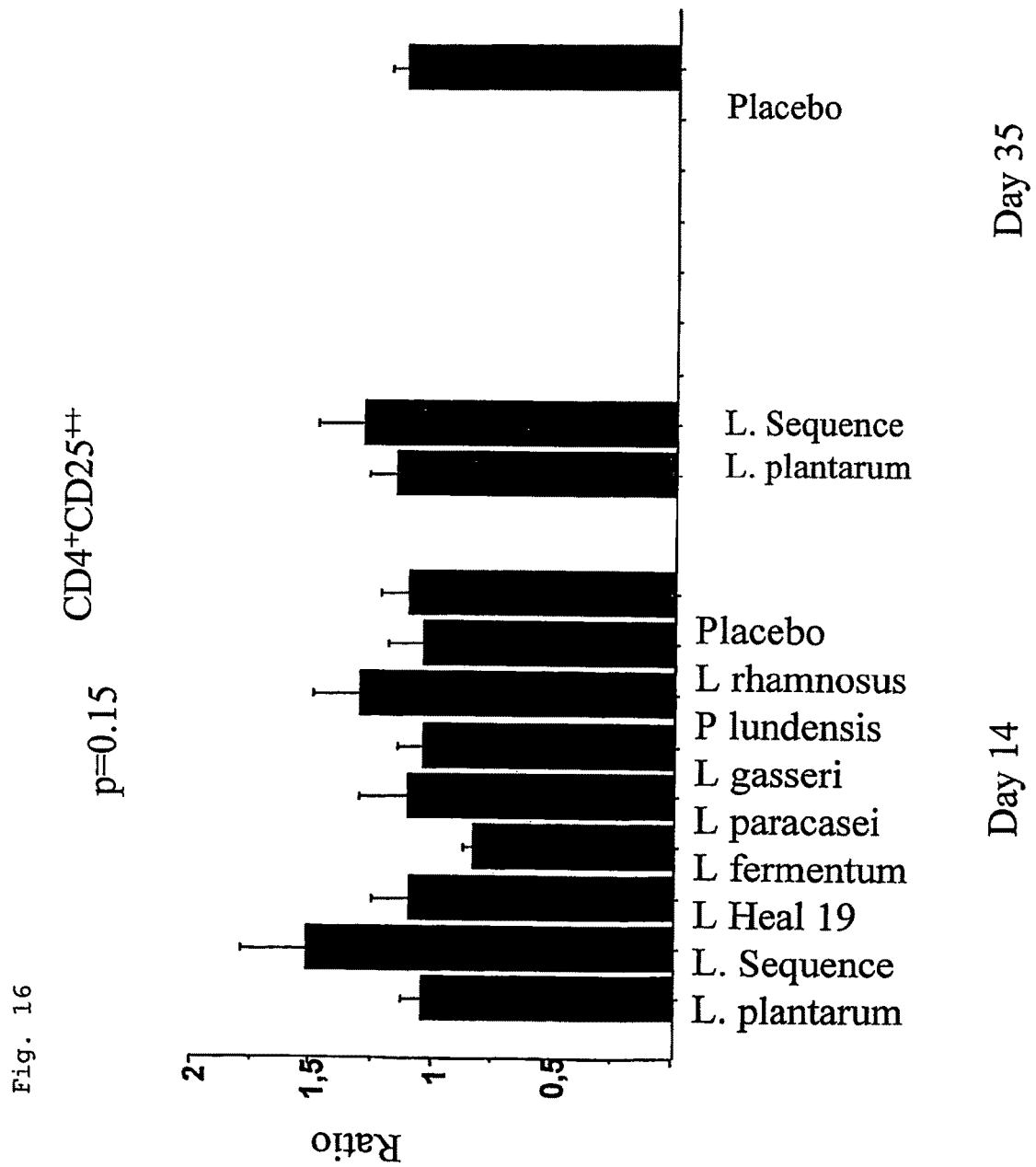
FIG. 16 shows the ratio of lymphocytes expressing the activation phenotypes $CD4^+CD25^{++}$ from experiment 2.
Figure 17:
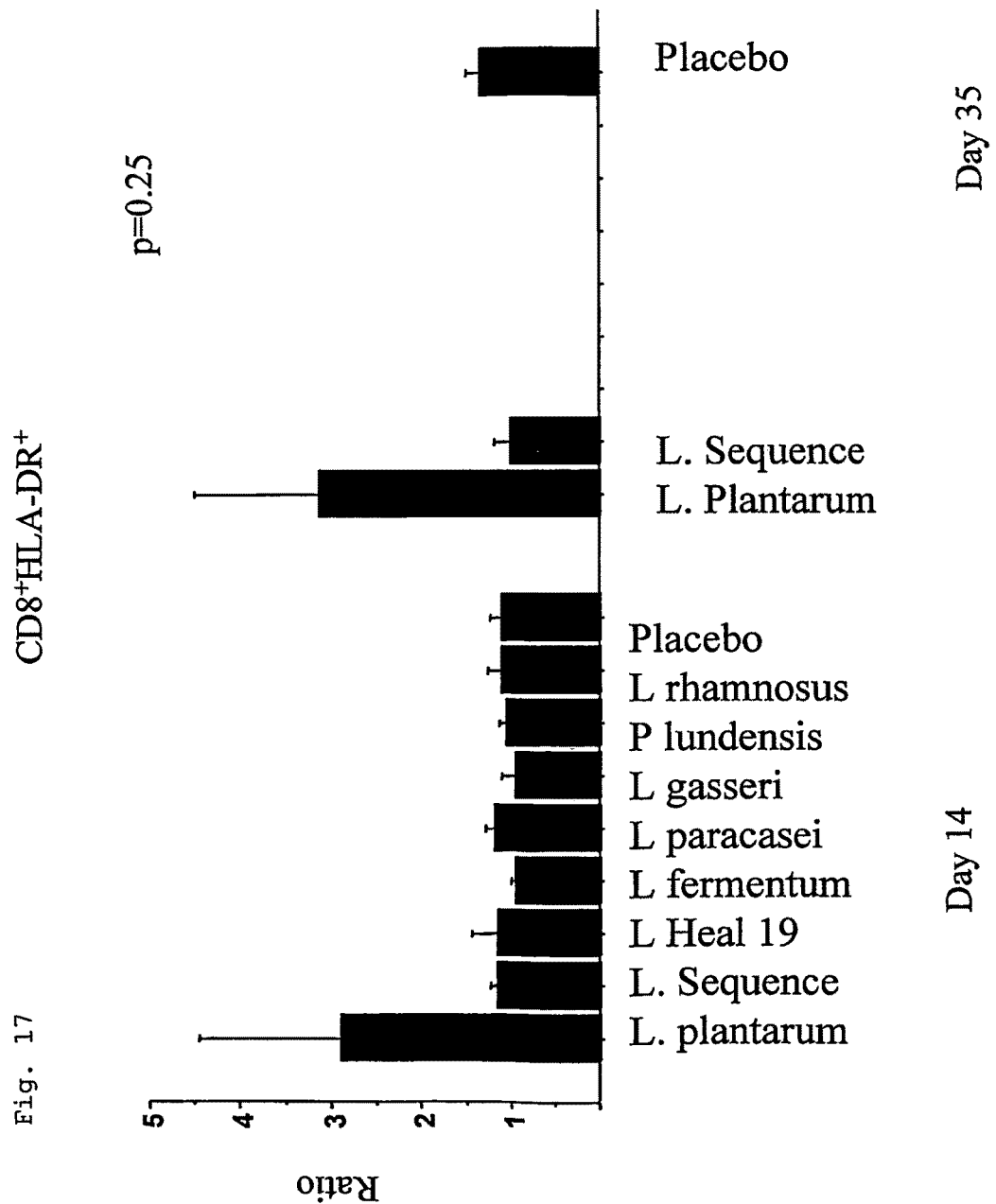
FIG. 17 shows the ratio of lymphocytes expressing the activation phenotypes $CD8^+HLA-DR^+$ from experiment 2.
Figure 18:
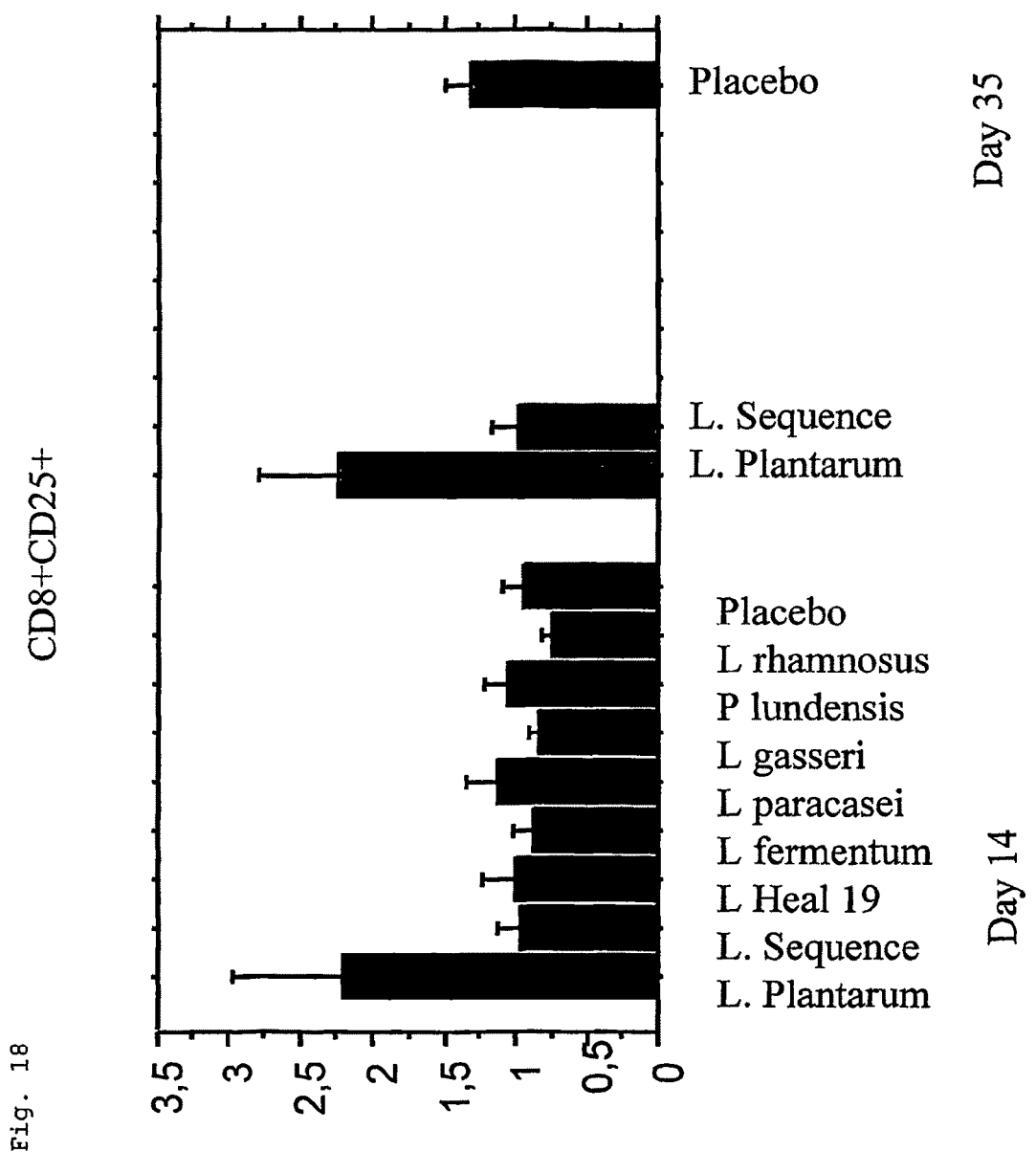
FIG. 18 shows the ratio of lymphocytes expressing the activation phenotypes $CD8^+CD25^+$ from experiment 2.
Figure 19:
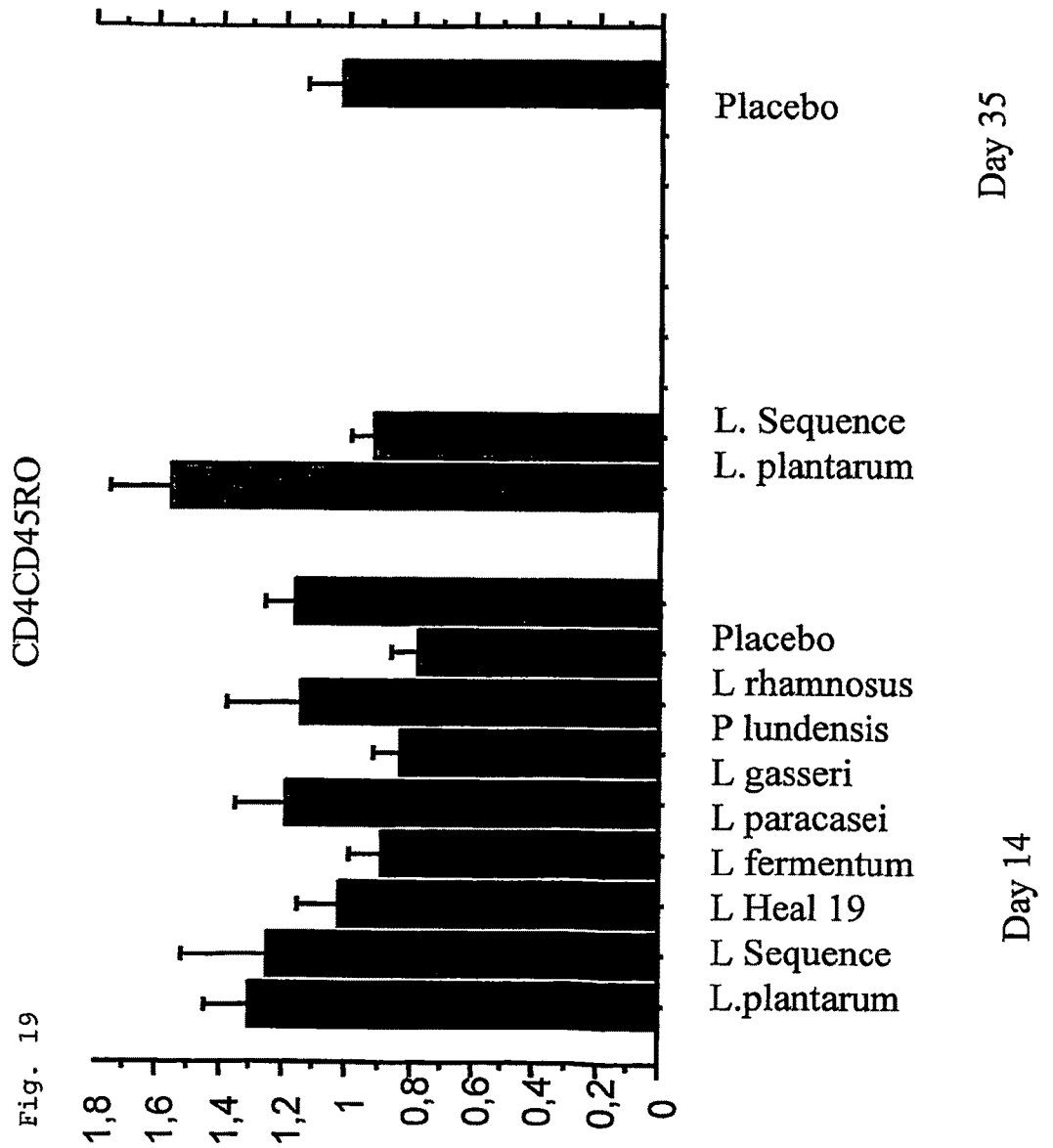
FIG. 19 shows the ratio of lymphocytes expressing the activation phenotypes CD4CD45RO from experiment 2.

The anti inflammatory mechanisms of the action of these treatments are still not known but our result clearly shows a key role of the $CD4^+CD25^+$ $Foxp3^+$ regulatory T cell population (see FIG. 14).

The invention claimed is:

1. A method of treating multiple sclerosis comprising administering to an individual having multiple sclerosis a sufficient amount of at least one isolated strain of probiotic *Lactobacillus* selected from the group consisting of *Lactobacillus plantarum* HEAL 9 deposited as DSM 15312, *Lactobacillus plantarum* HEAL 19 deposited as DSM 15313, and *Lactobacillus paracasei* 8700:2 deposited as DSM 13434.

2. The method of claim 1, wherein at least two of the strains of the probiotic *Lactobacillus* are administered to said individual.

3. The method of claim 2, wherein said at least two of the strains are administered in a sequence.

4. The method of claim 2, wherein said at least two of the strains are administered simultaneously.

5. A method of treating multiple sclerosis comprising administering to an individual having multiple sclerosis a sufficient amount of a combination of isolated strains of probiotic *Lactobacillus plantarum* HEAL 9 deposited as DSM 15312, *Lactobacillus plantarum* HEAL 19 deposited as DSM 15313, and *Lactobacillus paracasei* 8700:2 deposited as DSM 13434.

* * * * *

SEQUENCE LISTING

```
<160> NUMBER OF SEQ ID NOS: 1

<210> SEQ ID NO 1
<211> LENGTH: 21
<212> TYPE: PRT
<213> ORGANISM: Artificial Sequence
<220> FEATURE:
<223> OTHER INFORMATION: Synthetic Peptide
```

-continued

```
<400> SEQUENCE: 1

Met Glu Val Gly Trp Tyr Arg Ser Pro Phe Ser Arg Val Val His Leu
1               5                   10                  15

Tyr Arg Asn Gly Lys
            20
```